United States Patent [19]
Fossan et al.

[11] Patent Number: 5,531,769
[45] Date of Patent: Jul. 2, 1996

[54] TRUNCATED PULSE DEFIBRILLATOR WITH FLASH TUBE SWITCH

[75] Inventors: Helge Fossan, Stavanger, Norway; Jonathan M. Benson, Oregon City, Oreg.

[73] Assignee: Laerdal Manufacturing Corp., Tualatin, Oreg.

[21] Appl. No.: 366,664

[22] Filed: Dec. 29, 1994

[51] Int. Cl.⁶ .................................................. A61N 1/39
[52] U.S. Cl. ....................................................... 607/7; 607/5
[58] Field of Search ...................................... 607/5, 7, 74

[56] References Cited

U.S. PATENT DOCUMENTS

| | | | |
|---|---|---|---|
| 3,723,887 | 3/1973 | Panico | 607/5 |
| 3,773,050 | 11/1973 | Panico . | |
| 3,886,950 | 6/1975 | Ukkestad et al. | 607/5 |
| 4,850,357 | 7/1989 | Bach, Jr. | 607/7 |
| 5,222,492 | 6/1993 | Morgan et al. | 607/5 |

OTHER PUBLICATIONS

"The Objectives and Uses of AAMI Standards and Recommended Practices—Cardiac Defibrillator Devices," *Association for the Advancement of Medical Instrumentation*, 1989, 23 pp.

Primary Examiner—William E. Kamm
Assistant Examiner—Kennedy J. Schaetzle
Attorney, Agent, or Firm—Klarquist Sparkman Campbell Leigh & Whinston

[57] ABSTRACT

A defibrillator utilizes at least one flash tube for switching electrical energy from an energy source to a heart patient. The flash tube has a high impedance state in which the patient is isolated from the energy. In response to a triggering pulse, the flash tube enters a low impedance state in which energy is delivered to the patient. An additional switching element in the defibrillator operates to interrupt energy delivery through the flash tube so that a truncated defibrillation pulse having a desired energy level is produced.

25 Claims, 5 Drawing Sheets

TRUNCATED PULSE DEFIBRILLATOR WITH FLASH TUBE SWITCH

FIELD OF THE INVENTION

The present invention relates generally to heart defibrillation with truncated pulse wave forms, and more particularly relates to a defibrillator using a flash tube as a switching element.

BACKGROUND OF THE INVENTION

Heart tachyarrhythmias, including fibrillation, in a patient can be stopped by applying an electrical pulse to the patient, such as with a defibrillator. In general, defibrillators have comprised an electrical energy source and a pair of electrodes connected to the energy source with an electromechanical relay switch. The electrodes are placed in contact with the patient's chest, and the relay switch closed to deliver a high energy pulse to the patient. Prior defibrillators of this type suffer the disadvantage that the electromechanical relay switch has a comparatively slow switching time, and is subject to contact chatter.

In U.S. Pat. No. 3,773,050, Panico discloses using a gas-filled discharge flash tube as a fast acting, high energy switch in a defibrillator. The flash tube is non-conducting until a triggering pulse is applied to its control electrode. The flash tube then continues to conduct until electrical energy from a power source is discharged through the flash tube and patient to a particular voltage.

For effective heart defibrillation, application of a relatively precise amount of electrical energy to the patient can prove critical. Certain types of defibrillation pulse wave forms have also proven to be more beneficial. The ANSI/AAMI DF2-1989 standard provides specifications for two defibrillation pulse wave forms, a damped sinusoidal wave form and a truncated exponential wave form. The damped sinusoidal wave form is generally obtained by discharging a capacitor through a waveshaping inductor. The truncated exponential wave form is generally obtained by truncating a capacitor discharge. These wave forms have been proven in clinical studies to be highly effective in terminating heart fibrillations.

U.S. Pat. No. 4,823,796 to Benson, which is incorporated herein in its entirety by reference, is an example of a known defibrillator which delivers a truncated exponential or trapezoidal defibrillation pulse to a patient.

SUMMARY OF THE INVENTION

The present invention provides a defibrillator which controls delivery of a defibrillation pulse to a patient to have a selected energy amount and wave form. (In some embodiments of the invention, the defibrillator can deliver any of various energy amounts and wave forms.) In presently preferred embodiments of the invention, the defibrillator produces a defibrillation pulse with a truncated exponential wave form conforming to the ANSI/AAMI DF2-1989 standard.

The defibrillator according to the preferred embodiments of the invention comprises a flash tube serially coupled between an energy source and patient contactors (such as electrodes or the like). A control circuit initiates energy delivery by applying a triggering signal to the flash tube. An additional switching element is connected to interrupt energy delivery through the flash tube in response to a termination signal from the control circuit. The control circuit monitors the energy delivery during application of the defibrillation pulse to the patient, and applies the termination signal to the switching element to interrupt energy delivery through the flash tube such that a defibrillation pulse having a truncated exponential wave form and a selected energy amount is produced.

In one preferred embodiment of the invention, the defibrillator comprises dual flash tubes connecting the energy source and patient contactors. In another preferred embodiment, the defibrillator comprises a flash tube and a relay switch connecting the energy source and patient contactors. When not delivering a defibrillation pulse, the flash tubes or flash tube and relay switch provide electrical isolation of the patient from the energy source (i.e. the patient's electrical potential is "floating" with respect to that of the energy source).

An advantage to the defibrillators according to the preferred embodiments is that they provide an extremely short delay (a few microseconds in some embodiments of the invention) between application of the triggering pulse signal and the onset of energy delivery to the patient. Accordingly, these defibrillators can deliver defibrillation pulses which are more precisely synchronized with heart electrical activity.

Additional features and advantages of the invention will be made apparent from the following detailed description of a preferred embodiment which proceeds with reference to the accompanying drawings.

DETAILED DESCRIPTION OF THE PREFERRED EMBODIMENTS

Figure 1:
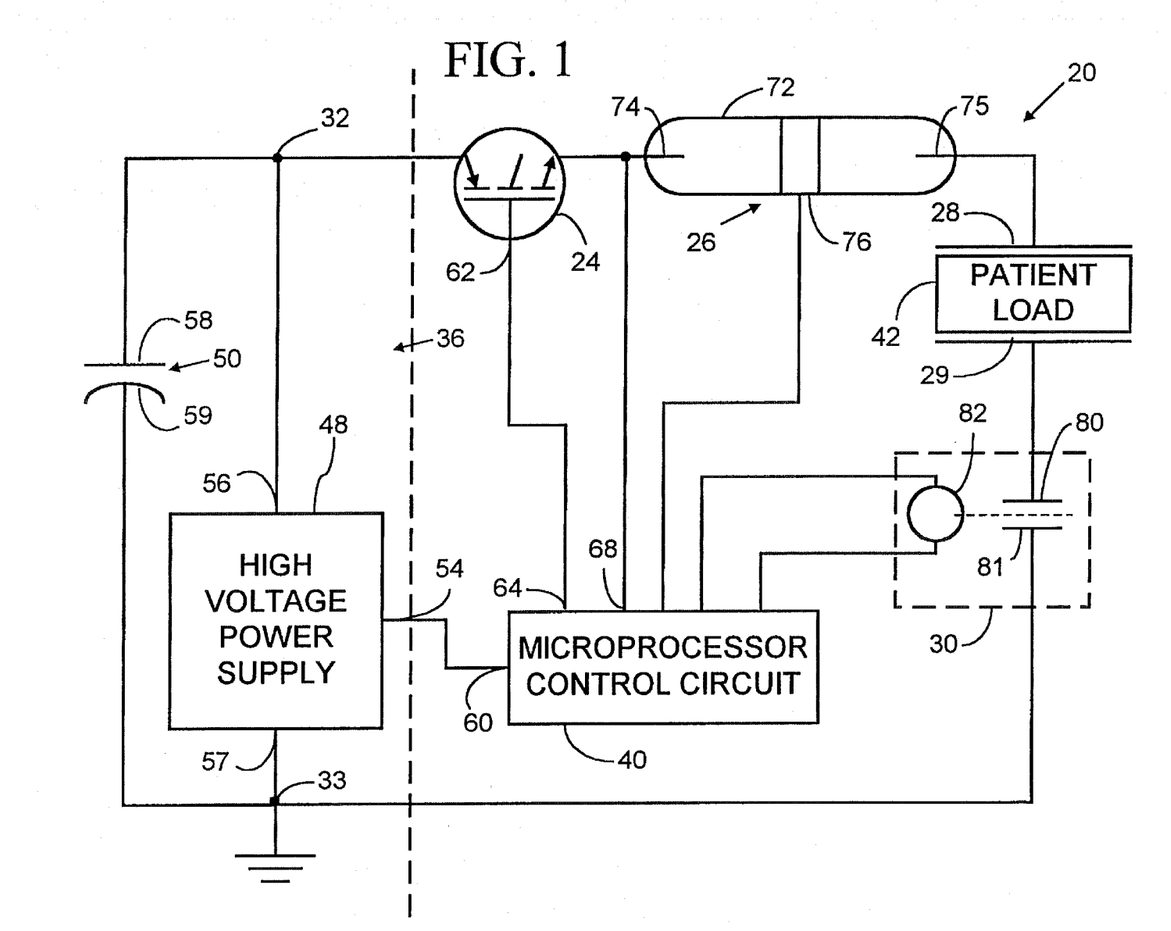
FIG. 1 is a circuit block diagram of a flash tube defibrillator circuit according to a first embodiment of the invention.

With reference to FIG. 1, a defibrillator 20 according to a first preferred embodiment of the invention comprises a switching element 24 such as a semiconductor current switch, a flash tube 26, patient contactors 28–29, and an electro-mechanical relay switch 30 connected in series between positive and negative terminals 32–33, respectively, of an energy source 36. A control circuit 40 controls the operation of the defibrillator circuit 20 to produce a defibrillation pulse having a desired energy level and wave form which is applied to a heart patient 42 with patient contactors 28–29.

Charge Phase

Under direction of the control circuit 40, the energy source 36 stores a predetermined amount of electrical energy in an initial or charge phase of operation. Preferably, the energy source 36 comprises a high voltage power supply 48 (such as a single-ended DC—DC switching converter) and a capacitor 50. Alternatively, a bank of capacitors can be used in place of the capacitor 50. The power supply 48 has a charge enable input 54 connected to the control circuit 40, and power connections 56–57 to positive and negative terminals 58–59 of the capacitor 50. When the control circuit 40 applies a "charge enable" signal to the charge enable input 54, the power supply 48 produces a charging current at power connections 56–57 to charge the capacitor 50 to a predetermined energy level. The control circuit 40 generates the "charge enable" signal at a charge enable output 60. The amount of energy to be stored in the capacitor 50 is dependent on the energy selected for the defibrillation pulse (e.g. 200, 300, 360 Joules). The level of stored energy is typically higher than that of the defibrillation pulse to compensate for the energy loss in the defibrillator circuit 20 (e.g. in the flash tube 26), and to achieve truncation of the defibrillation pulse wave form at a desired level.

To obtain a desired level of stored energy, the control circuit 40 monitors the voltage at the positive capacitor terminal 68. The control circuit 40 measures this voltage via input 68 by closing the switching element 24 during charging of the capacitor 50. Preferably, the switching element 24 is a semiconductor switch (such as a current gain bipolar transistor or "IGBT") which the control circuit 40 renders fully conducting ("closes") by applying an "on" signal at a gate 62 of the switching element. The control circuit 40 generates the "on" signal at an output 64. The control circuit 28 continues applying the enabling signal to the power supply 36 until the capacitor 50 attains a voltage appropriate to the desired energy level. Connecting the measurement input 68 to the positive terminal 58 through the switching element 24 further allows the control circuit 40 to detect failure of the switching element 24 during the charging phase (i.e. before a defibrillation pulse is produced and applied to the patient 42).

During the charging phase, the flash tube 26 and relay switch 30 remain in non-conducting, or high impedance states. In general, the flash tube 26 comprises a gas filled tube 72 with a pair of main electrodes 74–75 at opposing ends of the tube, and a centrally located control electrode 76, and may suitably be implemented with a DU7670 Zenon Gas flash tube available from Heimann GmbH of Germany. The main electrodes 74–75 of the flash tube 72 are connected to the switching element 24 and patient contact 28. The flash tube 26 does not conduct current between its main electrodes 74–75 until a triggering pulse is applied to its control electrode 76. The relay switch 30 comprises main contacts 80–81 and an armature coil 82, and may suitably be implemented with an RY160Z0L1 electromechanical relay switch distributed in the U.S. by Globetek, Inc. The main contacts 80–81 of the relay switch 30 are connected to the patient contact 29 and a negative terminal 59 of the capacitor 50. The relay switch 30 does not conduct current between the main contacts 80–81 until they are closed by application of a triggering signal to the armature coil 82. As the flash tube 26 and relay switch 30 are connected between the capacitor 50 and patient 42, this ensures that no leakage current flows from the capacitor to the patient, effectively providing electrical isolation of the patient from the energy source 36.

Energy Delivery Phase

Figure 2:
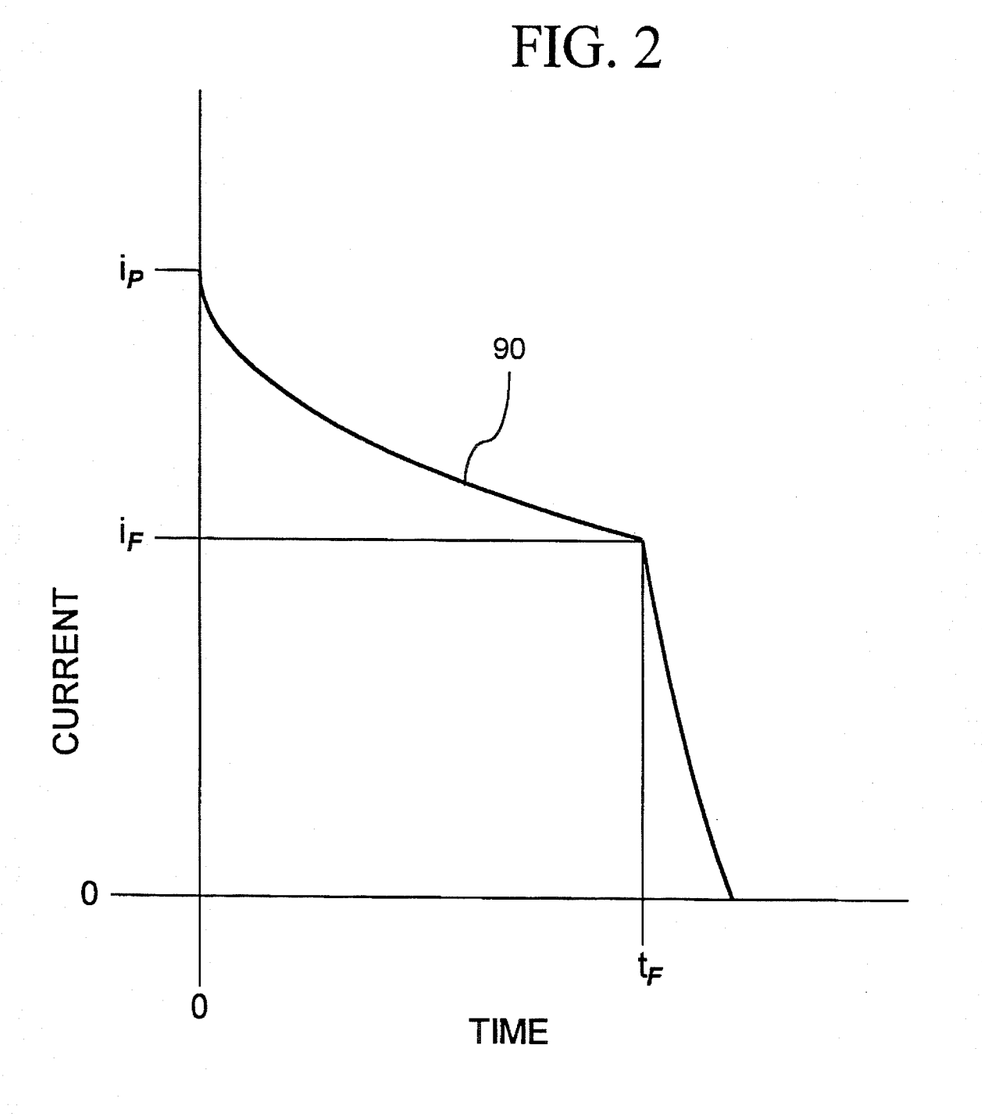
FIG. 2 is a graph of a truncated defibrillation pulse produced by the flash tube defibrillator circuit of FIG. 1.

Referring to FIGS. 1 and 2, with the capacitor 50 suitably charged, the defibrillator circuit 20 is ready to deliver a defibrillation pulse to the heart patient 30 in an energy delivery phase. Energy delivery is effected by creating a complete circuit from the positive capacitor terminal 58 through the switching element 24 and flash tube 26 to the patient 42, and back through the relay switch 30 to the negative capacitor terminal 59. To complete the circuit, the patient contactors 28–29 are placed in contact with the patient 42, and the switching element 24, flash tube 26, and relay 30 are brought to a low impedance, or conducting state. This results in the delivery of a defibrillation pulse to the patient.

More specifically, at the end of the charging phase, the flash tube 26 and relay 30 are in a non-conducting, high impedance state. The control circuit 40 initiates energy delivery to the patient 42 for heart defibrillation after the patient contactors 28–29 are placed in contact with the patient 42. The control circuit 40 maintains the switching element 24 in its conductive state after the charging phase by continuing to apply the on signal to the gate 62. The control circuit 40 then energizes the armature coil 82 of the relay switch 30 to close the relay switch's main contacts 80–81. This establishes an electrical connection of the patient 42 to the negative capacitor terminal 59. After the relay switch 30 is in a stable closed state, the control circuit 40 applies a triggering signal or pulse to the flash tube 26. With the high voltage of the capacitor 50 applied to the flash tube's main electrodes 74–75 and the control circuit's triggering signal applied to the control electrode 76, the flash tube 26 becomes conducting. With the switching element 24, flash tube 26, and relay switch 30 in low impedance states, current from the capacitor 50 flows through the circuit 20 and patient 42.

During energy delivery, the control circuit 28 continuously measures the capacitor voltage at its measurement input 68 (between the juncture of the switching element 24 and the flash tube 26). When the capacitor voltage drops to a voltage signifying that the required energy level of the defibrillation pulse has been obtained, the control circuit 40 truncates the defibrillation pulse wave form 90 (at time $t_F$ in FIG. 2) by terminating the on signal applied at the gate 62 of the switching element 24, causing the switching element to become non-conductive (i.e. "open" circuit). This halts the current flow through the flash tube 26 causing the flash tube to revert to a high impedance state. As a result, a defibrillation pulse having a truncated exponential wave form 90 (FIG. 2) conforming to the ANSI/AAMI DF2-1989 standard. Shortly thereafter, the control circuit 40 de-energizes the armature coil 82 to open the relay switch 30. Whereupon, the flash tube 26 and relay switch 30 prevent the flow of current between the capacitor 50 and patient 42, again electrically isolating the patient from the energy source 36.

Control and Measurement Circuit

Figure 3:
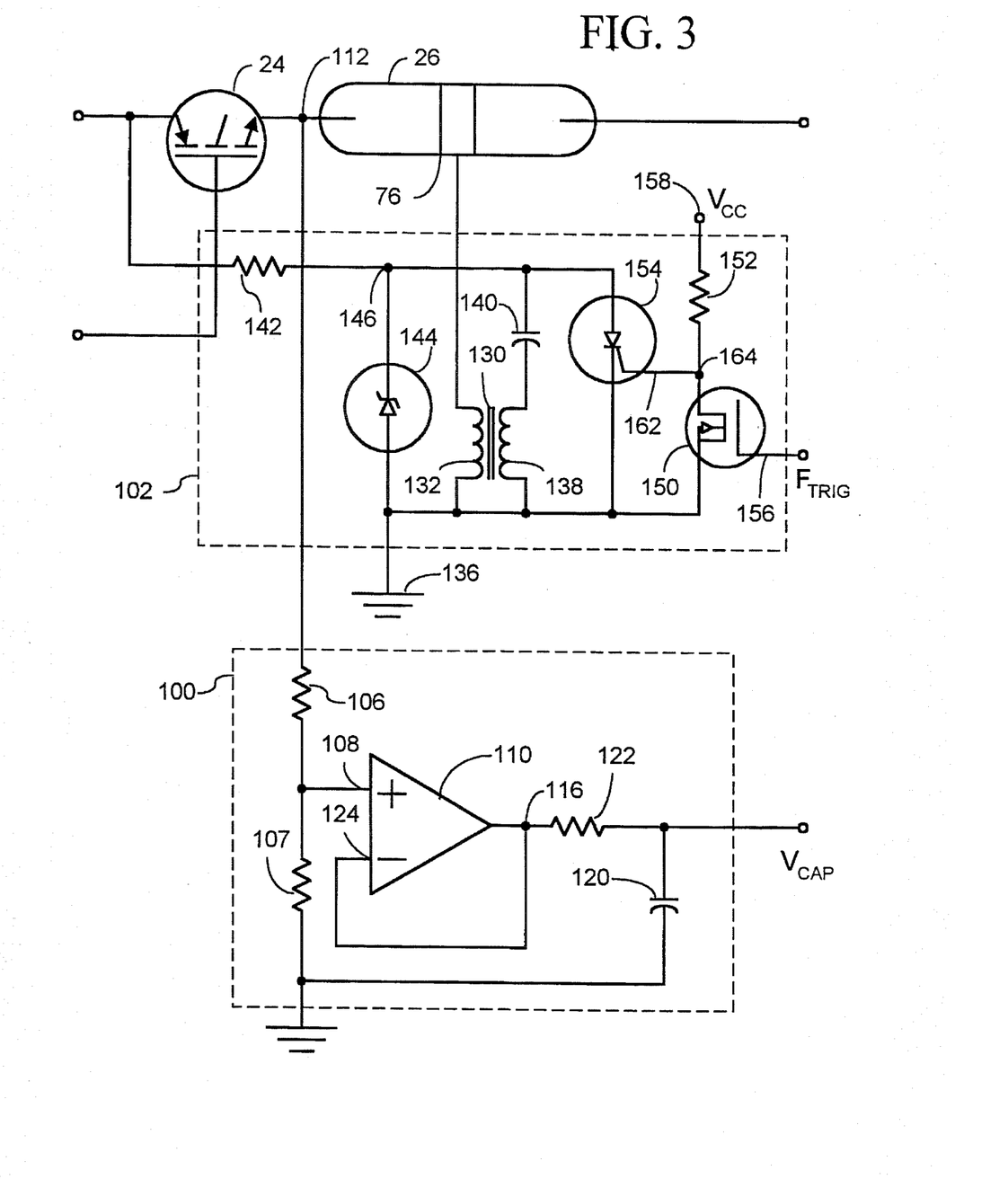
FIG. 3 is a circuit schematic diagram of a portion of a control circuit in the flash tube defibrillator circuit of FIG. 1.

Referring to FIG. 3, the control circuit 28 of the defibrillator 20 (FIG. 1) is preferably implemented with a suitably programmed microprocessor (not shown), such as the 80188 or 80C188 microprocessors manufactured by Intel and other like microprocessors. To control energy delivery through the flash tube 26 during the energy delivery phase, the control circuit 28 also includes a capacitor voltage measurement circuit 100 and a flash tube triggering circuit 102. The measurement circuit 100 produces an input signal for the microprocessor which is related to the voltage of the capacitor 50 (FIG. 1). The triggering circuit 102 applies the triggering signal at the control electrode 76 of the flash tube 26 responsive to an output signal of the microprocessor to initiate energy delivery.

The measurement circuit 100 comprises resistors 106–107 which are connected in a voltage divider configuration. The resistors 106–107 couple a positive input 108 of an operational amplifier 110 to a junction 112 between the switching element 24 and the flash tube 26. Accordingly, when the switching element 24 is closed in the charging and energy delivery phases, the positive terminal 58 of the capacitor 50 (FIG. 1) is connected to the positive input 108 of the operational amplifier 110 through the voltage divider resistors 106–107. The operational amplifier 110 has an output 116 which is coupled to a capacitor 120 through an output resistor 122, and to a negative input 124 of the operational amplifier. This produces a signal ($V_{CAP}$) related to the voltage of the capacitor 50 (FIG. 1) which is suitably scaled for input to the microprocessor.

The triggering circuit 102 operates to initiate energy delivery through the flash tube 26 by applying a trigger pulse to its control electrode 76 when enabled by the microprocessor. The triggering circuit 102 comprises a transformer 130 having a first winding 132 coupled between the control electrode 76 of the flash tube 26 and a circuit ground 136. A second winding 138 of the transformer 130 is coupled in series with a capacitor 140, and a resistor 142 between a positive terminal 58 of the capacitor 50 (FIG. 1) and the circuit ground 136. A zener diode 144 connects the circuit ground 136 to the juncture of the capacitor 140 and the resistor 142. The transformer 130 and associated circuit elements 140, 142 and 144 operate to drive the flash tube control electrode 76 with a triggering pulse when enabled by the output signal $F_{TRIG}$ from the microprocessor.

A transistor switch 150, a resistor 152 and a voltage controlled diode 154 are configured to enable and disable the triggering circuit 102 responsive to the output signal $F_{TRIG}$ which is applied at a gate input 156 of the transistor switch 150. The transistor switch 150 and the resistor 152 are serially connected between a power supply voltage bus $V_{CC}$ 158 and the circuit ground 136. A control input 162 of the diode 154 is connected to a junction 164 of the transistor switch 150 and the resistor 152. When the output signal $F_{TRIG}$ is asserted, the diode 154 is turned off. This allows current from the capacitor 50 to be conducted through the transformer's first winding 132 so that the triggering pulse is generated in the second winding 138 and applied to the flash tube control electrode 76.

Alternative Embodiments

Figure 4:
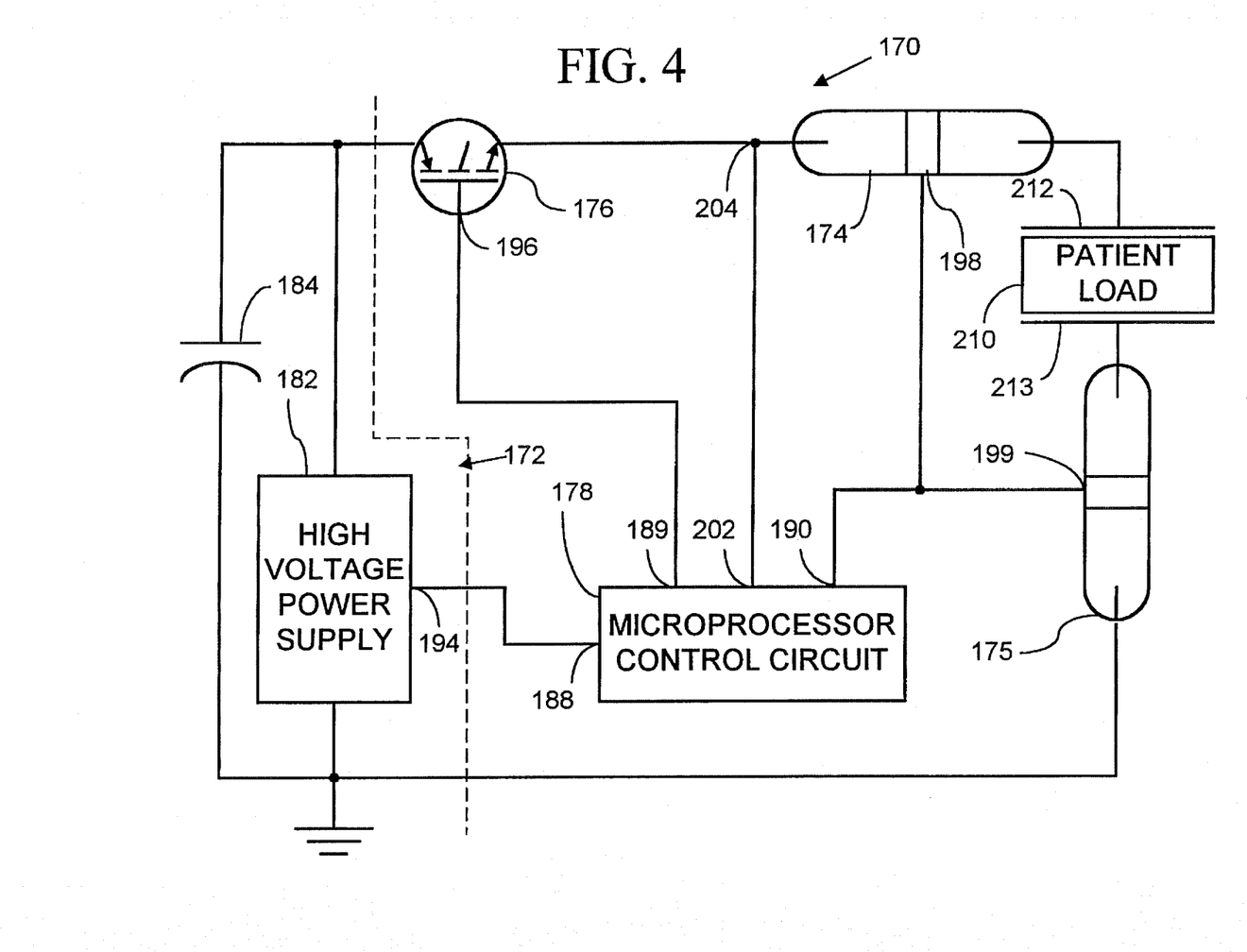
FIG. 4 is a circuit block diagram of a flash tube defibrillator according to a second embodiment of the invention.

With reference to FIG. 4, a defibrillator circuit 170 according to an alternative embodiment of the invention comprises an energy source 172, a pair of flash tubes 174, 175, a switching element 176, and a control circuit 178. The control circuit 178 includes flash tube triggering and voltage monitoring circuits such as shown in FIG. 3. The energy source 172 preferably comprises a high voltage power supply 182 and a capacitor 184. The control circuit 178 has outputs 188–190 connected to a charge enable input 194 of the power supply 182, a gate input 196 of the switching element 176, and to control electrodes 198–199 of the flash tubes 174–175, respectively. The control circuit 178 also has an input 202 connected at a measurement node 204 between the switching element 176 and flash tube 174. The control circuit 178 controls the operation of the defibrillator circuit 170 to produce a defibrillation pulse having a desired energy level and wave form which is applied to a heart patient 210 with patient contactors 212–213.

Before applying a defibrillation pulse patient, the capacitor 184 is charged to a level of electrical energy which again is typically higher than the amount of energy to be delivered to the patient 210 to compensate for energy loss in the defibrillator circuit 170, and achieve truncation of the defibrillation pulse at a desired voltage level. Charging of the capacitor 184 is effected by the control circuit 178 applying a charge enable signal to the charge enable input 194. The power supply 182 then generates a charging current which is applied to the capacitor 184. The control circuit 178 also closes the switching element 176 by applying an "on" signal to its gate input 196 so that the energy level of the capacitor 184 can be monitored by measuring the voltage at the measurement node 204. When the capacitor 184 has been charged to the desired energy level, the control circuit 178 interrupts the charge enable signal to shut off the charging current.

During charging, the flash tubes 174–175 are held in a non-conductive or high impedance state by the control circuit 178 applying appropriate electrical signals to the control electrodes 198–199. In this state, the flash tubes prevent the flow of current between the capacitor 184 and the patient 210, thus maintaining electrical isolation between the patient and the energy source 172.

To deliver a defibrillation pulse with a truncated exponential waveform 90 (FIG. 2) to the patient 210, the patient contactors 212–213 are placed on the patient. The control circuit 178 continues to apply the on signal to the gate 196 of the switching element 176 so that the switching element remains in its conducting state. The control circuit 178 then initiates the defibrillation pulse by applying a triggering pulse signal to the flash tubes 174–175 which causes the flash tubes to enter a low impedance or conductive state. With the switching element 176 and flash tube 174–175 all in low impedance states, current flows between the capacitor 184 and the patient 210.

During energy delivery, the control circuit 178 continuously measures the voltage of the capacitor 184 at the measurement node 204. When a voltage is attained that signifies the desired amount of energy has been delivered to the patient 210, the control circuit 178 applies an off signal to the gate input 196 to place the switching element 176 in a non-conducting state. This terminates current flow to the patient 210, thereby truncating the defibrillation pulse. The flash tubes 174–175 also become non-conductive. With the flash tubes 174–175 in their non-conductive states, the patient 210 is again electrically isolated from the energy source 172.

Figure 5:
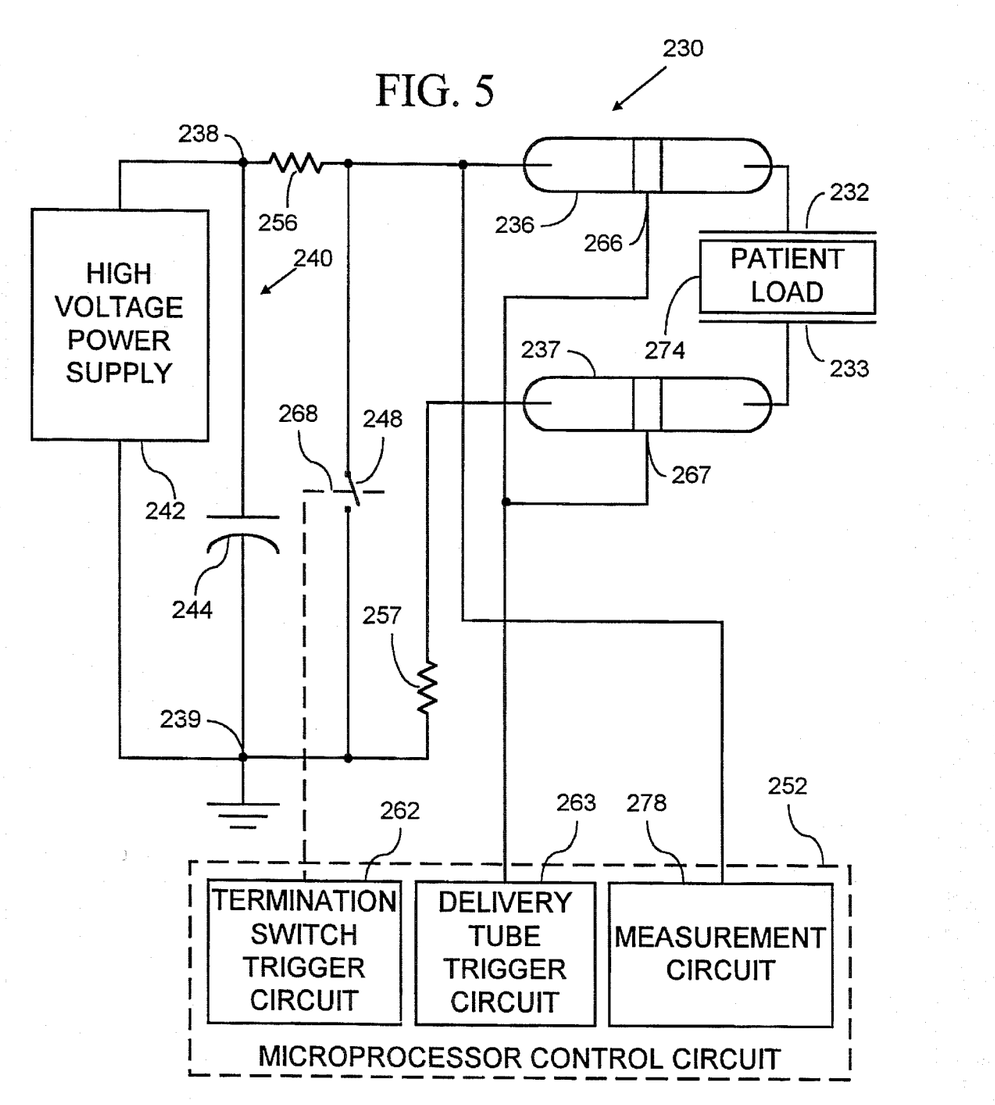
FIG. 5 is a circuit block diagram of a flash tube defibrillator according to a third embodiment of the invention.

With reference to FIG. 5, in a defibrillator 230 according to a further alternative embodiment of the invention, a pair of patient contactors 232–233 are connected with flash tubes (the "delivery flash tubes") 236–237 to positive and negative terminals 238–239, respectively, of an energy source 240. The energy source 240 preferably comprises a high voltage power supply 242 and a capacitor 244. A switching element (the "termination switching element") 248 also connects the positive and negative energy source terminals 238–239. A control circuit 252 operates to control the delivery of a defibrillation pulse by the defibrillator 230. Two resistors 256–257 also are connected in series with the delivery flash tubes 236–237 and patient contactors 232–233 between the positive and negative energy source terminals 238–239.

The termination switching element 248 can be a flash tube, electromechanical relay, semiconductor switch, or other electrical switching device. Due to the impedance of flash tubes in their low impedance or on states, the defibrillator 230 may not produce a precisely truncated exponential waveform when a flash tube is used as the termination switching element 248. Accordingly, low on-state impedance switching devices, such as an electromechanical relay, transistor, or thyristor, are preferred for implementing the termination switching element 248 of the defibrillator 230. An electromechanical relay is considered best suited of these alternatives for use as the termination switching element 248.

The control circuit 252 includes separate triggering circuits 262–263 for the termination switching element 248 and the delivery flash tubes 236–237. During charging, the delivery flash tubes 236–237 are each kept in a non-conducting or high impedance state by the trigger circuit 263 of the control circuit 252 applying an appropriate voltage at control electrodes 266–267 of the flash tubes. The termination switching element 248 also is kept in a non-conducting state by the trigger circuit 262 applying a voltage at a control input 268 of the element 248. With the delivery flash tubes 236–237 in this state, the patient contactors are electrically isolated from the energy source 240. The power supply 240 then applies a charging current to the capacitor 244 to store electrical energy for the defibrillation pulse therein. The control circuit 252 controls the amount of energy stored in the capacitor 244 to be typically higher than that of the desired defibrillation pulse so as to compensate for energy loss in the defibrillator 230, and to permit truncation of the defibrillation pulse at a desired level.

When the capacitor 244 is sufficiently charged, as determined by measurement circuit 278 which may include a circuit 100 shown in FIG. 3, the defibrillator 230 can deliver a defibrillation pulse to a patient 274. To deliver the defibrillation pulse, contact with the patient 274 is made using the patient contactors 232–233. The triggering circuit 263, which may be a circuit 102 shown in FIG. 3, in the control circuit 252 then applies a triggering pulse signal to the delivery flash tubes 182–183, whereupon the delivery flash tubes enter a conducting or low impedance state. With the delivery flash tubes 236–237 in the low impedance state, electrical current flows through the patient 274 between the positive and negative energy source terminals 238–239.

During energy delivery, a measurement circuit 278 in the control circuit 252 monitors the voltage on the capacitor 244 and maintains the termination switching element 248 in a high impedance state. When the voltage measurement indicates that the desired energy delivery has been achieved, the triggering circuit 262 terminates the defibrillation pulse by applying a triggering signal to the termination switching element 248 to place the termination switching element in a low impedance state where current from the capacitor 244 is shunted through the termination switching element. In the case of the termination switching element 248 being implemented as a flash tube, the triggering circuit 262 may be the circuit 102 shown in FIG. 3. Because the current path through the delivery flash tubes 182–183 and patient 212 has a higher impedance than that through the termination switching element 196 in its low impedance state, the current through the delivery flash tubes 236–237 is reduced. When the current through the delivery flash tubes 236–237 falls below a sustainable level, the delivery flash tubes return to a high impedance state. This results in the defibrillation pulse being truncated at the desired energy level.

Having described and illustrated the principles of our invention with reference to a number of preferred embodiments, it will be recognized that the preferred embodiments can be modified in arrangement and detail without departing from such principles. For example, the defibrillator 20 of the first preferred embodiment can alternatively be implemented with a semiconductor switch or the like in place of the relay switch 30. In view of the many possible embodiments to which the principles of our invention may be put, it should be recognized that the detailed embodiments are illustrative only and should not be taken as limiting the scope of our invention. Rather, we claim as our invention all such embodiments as may come within the scope and spirit of the following claims and equivalents thereto.

We claim:

1. A circuit for terminating heart tachyarrhythmias, comprising:
   an energy source having positive and negative terminals, and having stored electrical energy;
   first and second patient contactors for making contact with a patient;
   at least one delivery flash tube having a pair of main electrodes and a control electrode, the main electrodes of the delivery flash tube being coupled in series with the patient contactors between the positive and negative terminals of the energy source;
   a delivery control circuit connected to the control electrode of the delivery flash tube for applying a triggering pulse to said control electrode so that electrical current from the energy source is conducted through the delivery flash tube and patient; and
   switching means for interrupting the electrical current through the delivery flash tube, whereby a defibrillation pulse applied to the patient is truncated.

2. The circuit of claim 1 including first and second delivery flash tubes each having a pair of main electrodes and a control contactor, the main electrodes of the first delivery flash tube being coupled to the positive energy source terminal and the first patient contactor, the main electrodes of the second delivery flash tube being connected to the negative energy source terminal and the second patient contactor wherein the delivery control circuit is connected to the control electrodes of the delivery flash tubes for applying a triggering pulse to each of said control electrodes so that electrical current from the energy source is conducted through the delivery flash tubes and patient; and wherein the switching means comprises means for interrupting the electrical current through each of the delivery flash tubes, whereby a truncated defibrillation pulse is applied to the patient.

3. The circuit of claim 1 wherein the switching means comprises:
   a semiconductor switch coupled in series with the at least one delivery flash tube and patient contactors between the positive and negative energy source terminals and having a control terminal, the semiconductor switch opening a connection between said energy source and said delivery flash tube responsive to a control signal applied to the control terminal whereby electrical current through the at least one delivery flash tubes is interrupted; and
   a termination control circuit connected to the control terminal of the semiconductor switch for applying the control signal.

4. The circuit of claim 1 wherein the switching means comprises:
   a termination switching element coupled to the positive and negative energy source terminals in parallel to the series connected at least one delivery flash tube and patient contactors, and having a control input; and
   a termination control circuit connected to the control input of the termination switching element for applying a triggering pulse to said control input to shunt electrical current from the energy source through the at least one termination switching element whereby electrical current through the at least one delivery flash tube is interrupted.

5. The circuit of claim 1 comprising:
   a termination control circuit including means for monitoring a defibrillating voltage supplied by the energy source to the delivery flash tubes, and for applying a control signal to the switching means to interrupt the electrical current through the delivery flash tubes.

6. The circuit of claim 5 wherein the switching means comprises a second flash tube in parallel with the series connected at least one delivery flash tubes and the patient contactors.

7. The circuit of claim 5 including first and second series connected delivery flash tubes each having a control electrode connected to the delivery control circuit, the delivery control circuit applying the triggering signal to the control electrodes of the first and second delivery flash tubes to initiate the flow of electrical current through the patient.

8. The circuit of claim 1 comprising:

a delivery switching element coupled in series with the at least one delivery flash tube and patient contactors between the energy source terminals, the delivery flash tube being connected between the first patient contactor and a first of the energy source terminals, the delivery switching element being coupled between the second patient contactor and a second of the energy source terminals, the delivery switching element and the delivery flash tube being operative to disconnect the patient contactors from the energy source terminals to provide electrical isolation of the patient from the energy source.

9. The circuit of claim 8 wherein the delivery switching element is an electromechanical relay switch.

10. The circuit of claim 9 wherein the relay switch has an armature coil connected to the delivery control circuit, the delivery control circuit applying an actuating signal to the armature coil to close the relay switch for delivery of electrical current to the patient and to open the relay switch for electrical isolation of the patient from the energy source.

11. The circuit of claim 8 wherein the delivery switching element comprises a second delivery flash tube.

12. A heart defibrillator comprising:

a capacitor for storing electrical energy and having first and second terminals;

first and second patient contacting electrodes;

a delivery flash tube having first and second conducting terminals coupled to the first capacitor terminal and the first patient contacting electrode, respectively, and having a control terminal;

a termination switch for interrupting defibrillation current flow through the delivery flash tube in response to a termination signal; and a control circuit connected to the delivery flash tube control terminal for applying a triggering signal to the delivery flash tube control terminal to initiate current flow through the delivery flash tube to deliver a defibrillation pulse to a patient, and connected to the termination switch for applying a termination signal to the termination switch whereby the defibrillation pulse is truncated.

13. The heart defibrillator of claim 12 further comprising:

a relay switch connecting the second capacitor terminal and second patient electrode, and having a control input connected to the control circuit, the relay switch opening in response to a signal from the control circuit to electrically isolate the patient from the capacitor, and closing in response to a signal from the control circuit to permit defibrillation current flow through the relay switch and the patient.

14. The heart defibrillator of claim 12 further comprising:

a second delivery flash tube having first and second conducting terminals coupled to the second capacitor terminal and the second patient contacting terminal, respectively, and having a control terminal connected to the control circuit;

the control circuit applying a triggering signal to the control terminal of the second delivery flash tube to initiate defibrillation current flow through the delivery flash tubes and the patient.

15. The heart defibrillator of claim 12 wherein the control circuit has an input for receiving a measurement signal related to an energy level of the defibrillation pulse, the control circuit applying the termination signal to the termination switch in response to the measurement signal to truncate the defibrillation pulse at a predetermined energy level.

16. The heart defibrillator of claim 12 wherein the control circuit comprises a microprocessor.

17. The heart defibrillator of claim 15 wherein the termination switch comprises:

a semiconductor switch connecting the first capacitor terminal and the first conducting terminal of the delivery flash tube, and having a control input connected to the control circuit for receiving the termination signal.

18. The heart defibrillator of claim 17 further comprising:

a relay switch connecting the second capacitor terminal and second patient electrode, and having a control input connected to the control circuit, the relay switch opening in response to a signal from the control circuit to isolate the patient, and closing in response to a signal from the control circuit to permit defibrillation current flow through the relay switch and the patient.

19. The heart defibrillator of claim 18 further comprising:

a second delivery flash tube having first and second conducting terminals coupled to the second capacitor terminal and the second patient contacting terminal, respectively, and having a control terminal connected to the control circuit;

the control circuit applying a triggering signal to the control terminal of the second delivery flash tube to initiate defibrillation current flow through the delivery flash tubes and the patient.

20. The heart defibrillator of claim 12 wherein the termination switch is connected in parallel to the capacitor for shunting current from the capacitor when the termination signal is applied.

21. The heart defibrillator of claim 20 further comprising:

a second delivery flash tube having first and second conducting terminals coupled to the second capacitor terminal and the second patient contacting terminal, respectively, and having a control terminal connected to the control circuit;

the control circuit applying a triggering signal to the control terminal of the second delivery flash tube to initiate defibrillation current flow through the delivery flash tubes and the patient.

22. A method for heart defibrillating, comprising:

storing electrical energy in a capacitor;

providing a conducting path for the electrical energy from a positive terminal of the capacitor through at least one flash tube, a patient, and back to a negative terminal of the capacitor;

applying a triggering signal to a control terminal of the flash tube to initiate current flow through the conducting path;

monitoring the electrical energy applied to the patient; and interrupting current flow through the conducting path responsive to the electrical energy monitoring whereby a truncated defibrillation pulse having a desired energy amount is applied to the patient.

23. The method of claim 22 wherein the interrupting step comprises:

applying a termination signal to a semiconductor switch in the conducting path to interrupt current flow through the conducting path whereby a truncated defibrillation pulse in applied to the patient.

24. The method of claim 22 wherein the interrupting step comprises:

shunting the electrical energy through a second conducting path between the positive and negative capacitor terminals.

25. The method of claim 22 in which the step of providing a conducting path comprises the step of providing such a path through a first flash tube, a patient, a second flash tube, and back to a negative terminal of the capacitor.

* * * * *